(12) United States Patent
Matula, Jr.

(10) Patent No.: US 10,124,139 B2
(45) Date of Patent: *Nov. 13, 2018

(54) PATIENT INTERFACE DEVICE WITH CHEEKBONE STABILIZATION

(75) Inventor: Jerome Matula, Jr., Apollo, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1019 days.

This patent is subject to a terminal disclaimer.

(21) Appl. No.: 13/583,074

(22) PCT Filed: Feb. 14, 2011

(86) PCT No.: PCT/IB2011/050609
§ 371 (c)(1),
(2), (4) Date: Sep. 6, 2012

(87) PCT Pub. No.: WO2011/110961
PCT Pub. Date: Sep. 15, 2011

(65) Prior Publication Data
US 2013/0037030 A1    Feb. 14, 2013

Related U.S. Application Data

(60) Provisional application No. 61/311,586, filed on Mar. 8, 2010.

(51) Int. Cl.
*A61M 16/06* (2006.01)
*A61M 16/08* (2006.01)

(52) U.S. Cl.
CPC .... *A61M 16/0683* (2013.01); *A61M 16/0605* (2014.02); *A61M 16/0666* (2013.01); *A61M 16/0816* (2013.01)

(58) Field of Classification Search
CPC .......... A61M 16/0683; A61M 16/0666; A61M 16/00; A61M 16/06; A61M 16/0605;
(Continued)

(56) References Cited

U.S. PATENT DOCUMENTS

| 5,117,818 A | * | 6/1992 | Palfy | ............... A61M 25/02 128/200.24 |
| 5,533,506 A | | 7/1996 | Wood | |

(Continued)

FOREIGN PATENT DOCUMENTS

| CN | 101516427 A | 8/2009 |
| JP | 2007510486 A | 4/2007 |

(Continued)

*Primary Examiner* — Justine Yu
*Assistant Examiner* — Douglas Sul
(74) *Attorney, Agent, or Firm* — Michael W. Haas

(57) ABSTRACT

A patient interface device (30, 230, 330, 430, 530, 630, 730) that includes a support member (34, 234, 334, 434, 534, 634) comprising a central support portion and of cheek mount supports (70) coupled to the central portion. Each cheek mount support is configured to apply a force a side a user's cheekbone while applying substantially no force over an apex of such a user's cheekbone responsive to the patient interface being worn by a user. A seal member (36, 236, 336, 436, 536, 636, 736) is coupled to the support portion. The seal member is adapted to seal against a surface of a user to communicate a flow of gas with an airway of such a user. A conduit coupling member (38, 355, 438a, 438b, 538) is coupled to the seal member.

11 Claims, 16 Drawing Sheets

(58) Field of Classification Search
CPC ........... A62B 9/04; A62B 18/00; A62B 18/02; A62B 18/04; A62B 18/08; A62B 18/084
See application file for complete search history.

(56) References Cited

U.S. PATENT DOCUMENTS

| | | | |
|---|---|---|---|
| 6,119,694 A * | 9/2000 | Correa et al. | 128/207.13 |
| 7,210,481 B1 | 5/2007 | Lovell | |
| 7,296,575 B1 * | 11/2007 | Radney | 128/207.11 |
| 7,878,200 B2 * | 2/2011 | Zollinger | A61M 16/0683 128/201.22 |
| 8,701,667 B1 * | 4/2014 | Ho et al. | 128/206.24 |
| 2003/0172936 A1 | 9/2003 | Wilkie | |
| 2005/0121030 A1 * | 6/2005 | Bateman et al. | 128/201.23 |
| 2006/0060200 A1 | 3/2006 | Ho | |
| 2008/0135050 A1 * | 6/2008 | Hitchcock | A61M 16/06 128/207.11 |
| 2008/0190432 A1 | 8/2008 | Blochlinger | |
| 2008/0245369 A1 | 10/2008 | Matula | |
| 2009/0044808 A1 | 2/2009 | Guney | |
| 2009/0126739 A1 | 5/2009 | Ng | |
| 2010/0307502 A1 * | 12/2010 | Rummery | A61M 16/06 128/205.25 |
| 2011/0067704 A1 * | 3/2011 | Kooij et al. | 128/207.18 |
| 2011/0083670 A1 * | 4/2011 | Walacavage | 128/205.12 |
| 2011/0197341 A1 * | 8/2011 | Formica | A61M 16/0683 2/209.3 |
| 2013/0074845 A1 * | 3/2013 | Smith | A61M 16/06 128/205.25 |

FOREIGN PATENT DOCUMENTS

| | | |
|---|---|---|
| WO | WO2005046776 A1 | 5/2005 |
| WO | WO2007041766 A1 | 4/2007 |
| WO | WO2007075491 A2 | 7/2007 |
| WO | WO2008007985 A1 | 1/2008 |
| WO | WO2008087468 A1 | 7/2008 |
| WO | WO2010073142 A1 | 7/2010 |

* cited by examiner

PATIENT INTERFACE DEVICE WITH CHEEKBONE STABILIZATION

CROSS-REFERENCE TO RELATED APPLICATIONS

This patent application claims the priority benefit under 35 U.S.C. § 371 of international patent application no. PCT/IB2011/050609, filed Feb. 14, 2011, which claims the priority benefit under 35 U.S.C. § 119(e) of U.S. Provisional Application No. 61/311,586 filed on Mar. 8, 2010, the contents of which are herein incorporated by reference.

BACKGROUND OF THE INVENTION

1. Field of the Disclosure

The present invention pertains to a patient interface device, and, in particular, to a patient interface device that includes cheek mount supports, which use the cheekbone to properly locate and fix the patient interface device on the face of the user.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient, to the airway of a patient/user. Typical pressure support therapies are provided to treat a medical disorder, such as sleep apnea syndrome, in particular, obstructive sleep apnea (OSA) or congestive heart failure and/or other medical and respiratory disorders, such as Cheynes-Stokes respiration, congestive heart failure, and stroke.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing a pressure support therapy to treat OSA, the patient normally wears the patient interface device all night long while he or she sleeps. Patient interface development has generally involved balancing of two competing goals: a) secure attachment to and seal with the user's face to create an airtight seal in order to facilitate the required positive airway pressure, and b) comfort to the user in order to maximize patient compliance, i.e., usage of the medical therapy. An airtight seal can be achieved by tightening the mask down firmly against the patient's face. However, this solution oftentimes results in discomfort to the user due to relatively high strapping forces needed to ensure a secure seal against the patient and less than satisfactory patient compliance. Alternatively, the mask may be fit loosely on the patient's face to enhance comfort. However, the effectiveness of the mask may be compromised if it is too loose.

A variety of masks have been suggested in the art seeking to address one or both of the above noted issues. For example, U.S. Patent Appln. Pub. No. 2006/0060200 A1 ("the '200 application") describes a patient interface that includes a support body having a cushion 34 and cheek interfaces 38. See FIG. 1 from the '200 application. Collectively, the cushion and cheek interfaces operate to distribute compressive forces exerted on the user's face. The support body of the patient interface is constructed from a flexible material to impart additional adjustability to the cheek supports. The cheek supports are designed to be disposed over a corresponding cheekbone of the user so that the interface is securely affixed on the face of the user. As discrete components, each cheek support may be moved independently relative to one another so that the patient interface may be easily customized for use with different user.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a support member comprising a central support portion and a pair of cheek mount supports (70) coupled to the central portion. Each cheek mount support is configured to apply a force a side a user's cheekbone while applying substantially no force over an apex of such a user's cheekbone responsive to the patient interface device being worn by a user. A seal member is coupled to the support portion. The seal member is adapted to seal against a surface of a user to communicate a flow of gas with an airway of such a user. A conduit coupling member is coupled to the seal member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
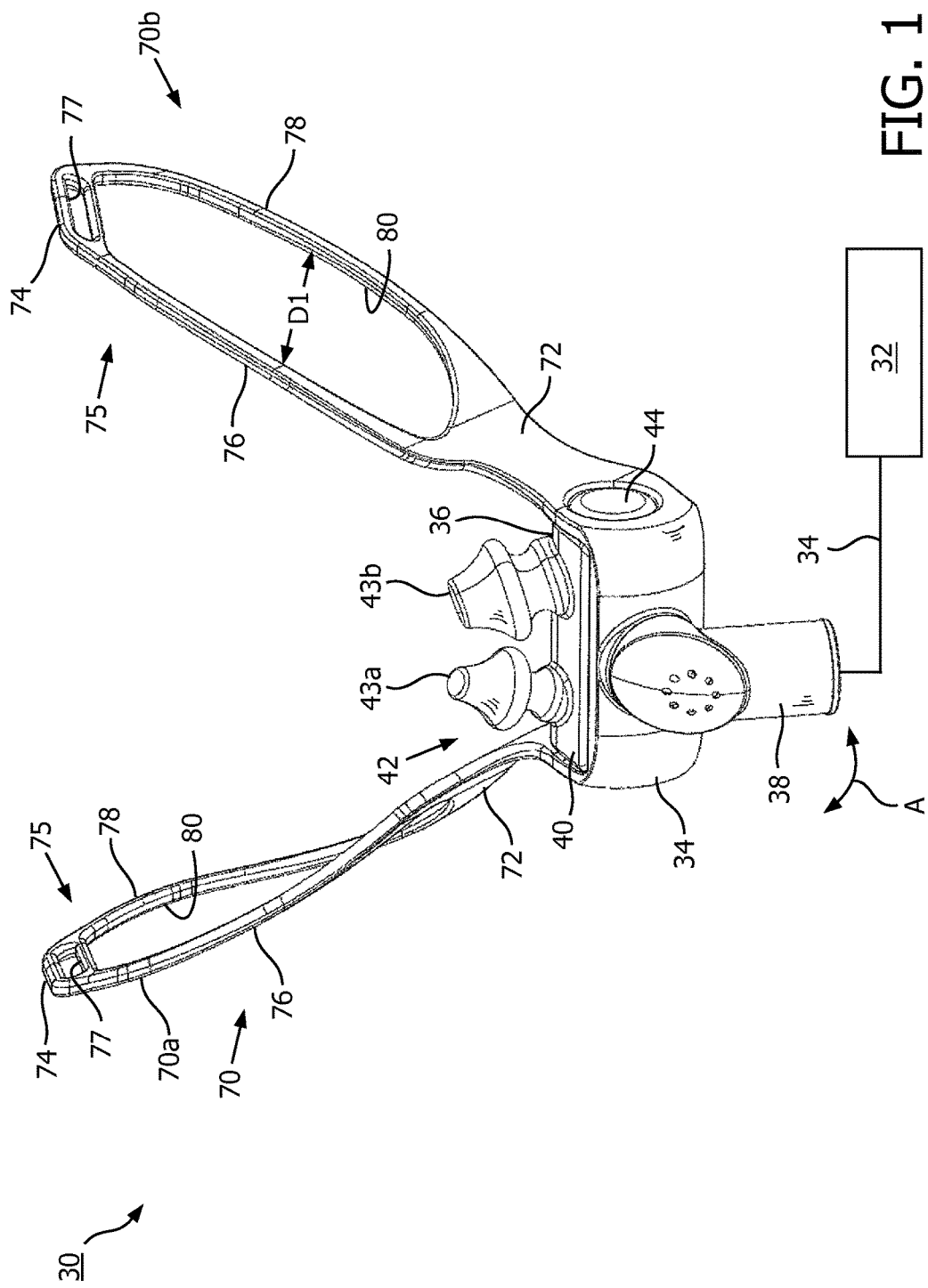
FIG. 1 is a front perspective view of a patient interface device according to a first embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
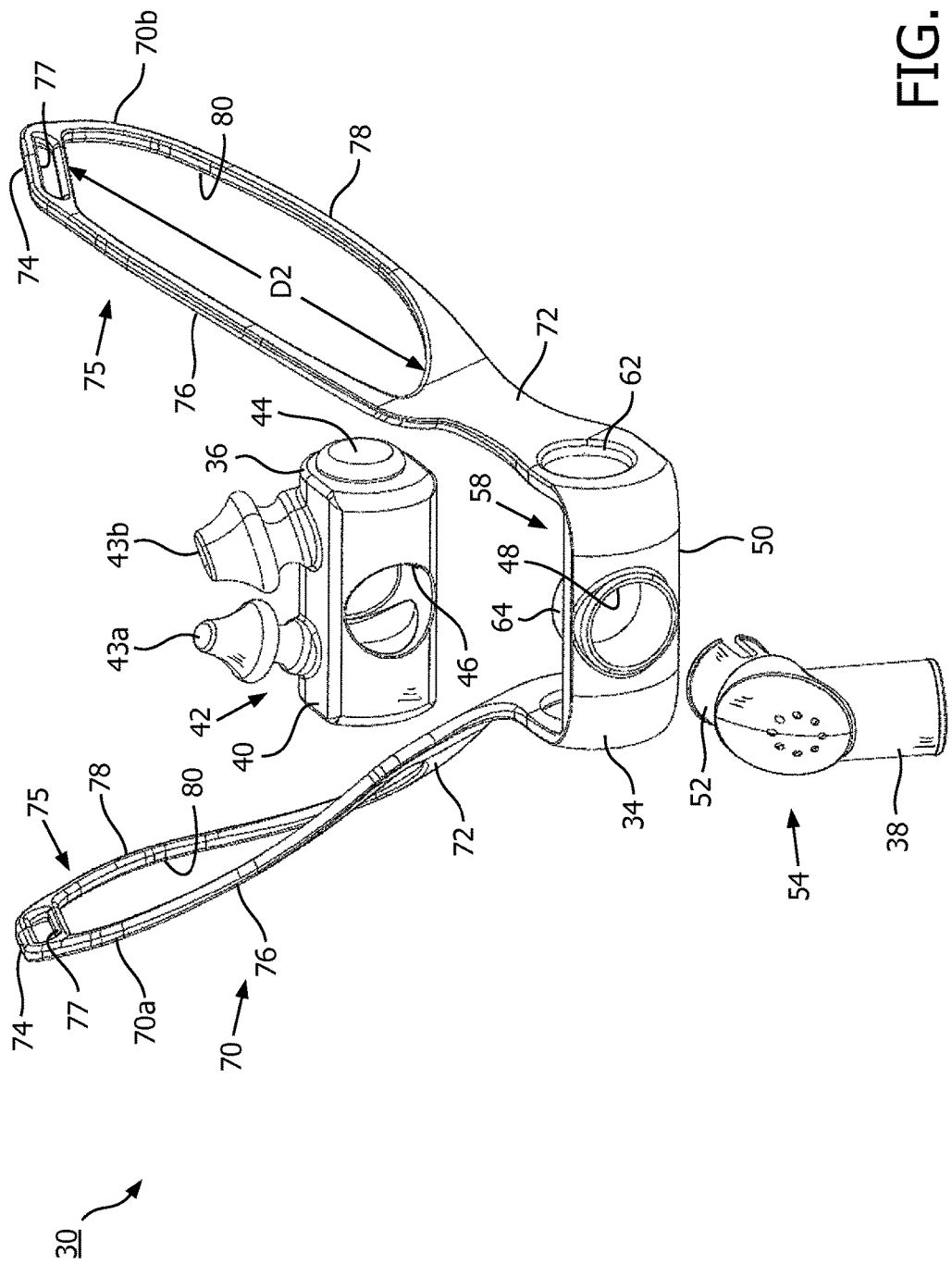
FIG. 2 is an exploded view of the patient interface device of FIG. 1.
Figure 3:
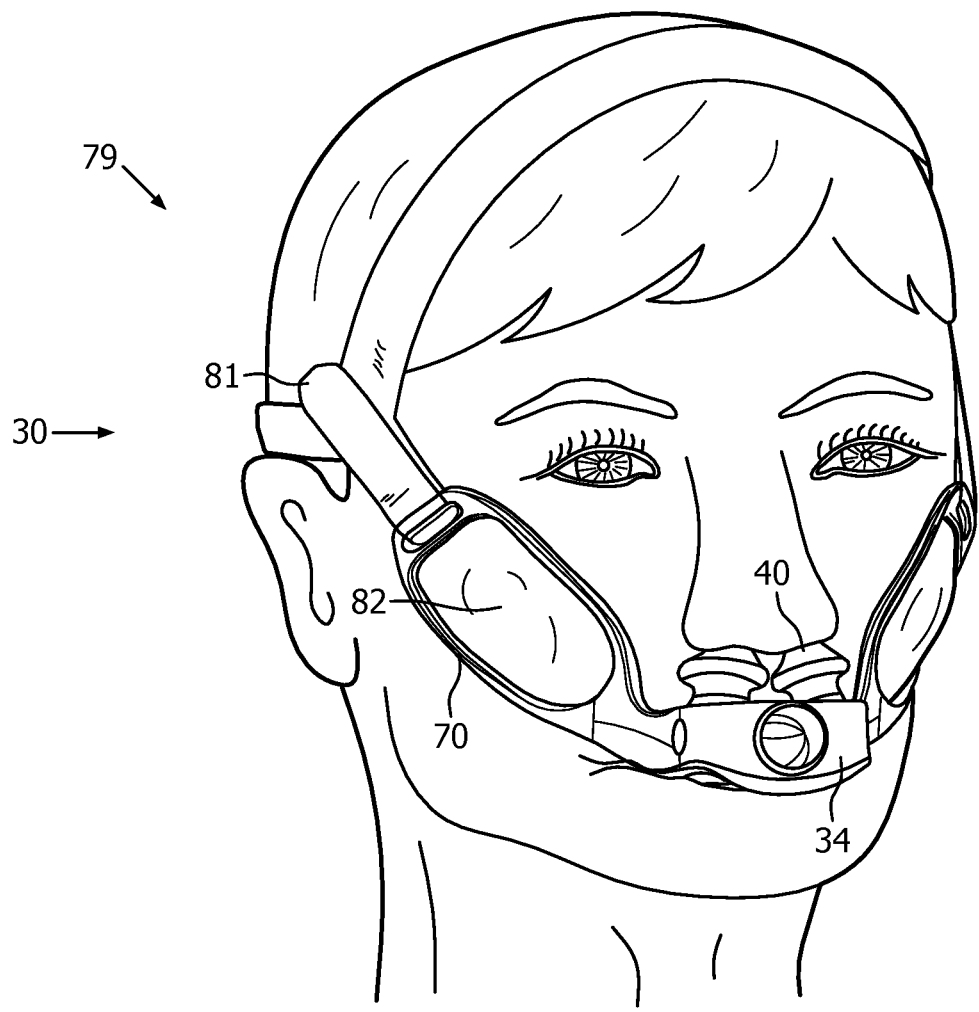
FIG. 3 is a front perspective view of the patient interface device of FIG. 1 shown worn by a user.

FIGS. 1-3 illustrate a first embodiment of a patient interface device 30 according to the principles of the present invention. Patient interface device 30 is shown schematically connected to a pressure support system 32 via a patient circuit 34, which communicates gas from the pressure support system to the patient interface device. Patient circuit 34 is any device, such as a flexible tubing, that carries the flow of gas from the pressure/flow generator in the pressure support system to the patient interface device.

Pressure support system 32 is any conventional ventilation or pressure support system. Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAPO) device, C-Flex device, Bi-Flex device, or a BiPAP® device manufactured and distributed by Philps Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening.

Patient circuit 34 can have any suitable configuration. For example, the patient circuit can be a single-limb tubing between the pressure support system and the patient interface device. Alternatively, the patient circuit can be a dual-limb tubing system; having an inspiratory limb for carrying a flow of gas to the user and a expiratory limb for carrying a flow of gas from the user. Typically, a Y-connector is provided near the patient that connects the inspiratory and expiratory limbs to the patient interface device.

It is to be further understood that various components may be provided in or coupled to pressure support system 32, patient circuit 34, patient interface device 30, or any combination thereof. For example, a bacteria filter, pressure control valve, flow control valve, pressure/flow/temperature/humidity sensor(s), meter, pressure filter, humidifier, and/or heater can be provided in or attached to the patient circuit.

Patient interface device 30 includes a support member 34, a seal member 36, and a conduit coupling member 38. In this illustrated exemplary embodiment, seal member 36 includes a seal body 40, a sealing element 42 coupled to the seal body, and coupling members 44 also coupled to the seal body. In this embodiment, the seal body, sealing element, and coupling members are defined from a unitary material such as silicon. It can be appreciated, however, that these components need not be formed from the same material. The present invention specifically contemplates that the sealing element and/or coupling members can be selectively attachable to the seal body.

In the illustrated exemplary embodiment, sealing element 42 is a pair of nasal prongs 43a and 43b, each of which seals against a respective nare of the user. Nasal prongs 43a and 43b are coupled to seal body 40 such that a flow of gas in the seal body is be delivered to the airway of the user. Nasal prongs 42a and 42b can be individually attachable to seal body 40 or they can be coupled to one another, for example, with a common connection to seal body 40 so that both can be removed from the seal body as a unitary structure. Moreover, the present invention contemplates that only one nasal prong can be provided so that gas is delivered to only one nare. Of course, nasal prongs 43a and 43b can have any one of a variety of configurations, shapes, sizes, and geometries.

The present invention contemplates that sealing element 42 can have other configurations and can be can be made from any suitable material, such as gel, silicone, foam, rubber, or combination of materials. For example, seal member 42 can be a nasal cushion that seals over both nares, a nasal/oral cushion that seals over the nose and mouth. Sealing element 42 need not be a structure that provides a seal with the user. For example, an oxygen cannula includes a distal end that is disposed in or near the nare but does not seal the airway. The present invention contemplate providing such a cannula as the sealing element.

Seal body 40 is a generally hollow structure that includes an opening 46 defined thereto to communicate a flow of gas with conduit coupling member 38. In the illustrated embodiment, only one opening is provided, but multiple openings are contemplates. Coupling members 44 are provided to assist in coupling and/or aligning the seal body to support member 34. In this illustrated embodiment, a single coupling member is provided at each end of seal body. The present invention contemplates providing coupling members at other locations on the seal body.

In the illustrated exemplary embodiment, conduit coupling member 38 is an elbow conduit coupled to an opening 48 defined in a central portion 50 of support member 34 such that the conduit coupling member 38 is rotatable relative to support member 34 as illustrated by arrow A. To achieve this coupling, conduit coupling member 38 includes a connecting portion 52 that inserts into opening 48. In an exemplary embodiment, the conduit coupling member is selectively attachable to support member 34, but it may also be permanently affixed thereto and need not be rotatably attached.

The present invention also contemplated providing an exhaust assembly, generally indicated at 54, in the conduit coupling member to allow gas, such as the patient's exhaled carbon dioxide, to exhaust to the ambient atmosphere. Exhaust assembly 54 can have any suitable configuration, such as one or more vent holes provided in the wall of conduit coupling member 38.

The present invention also contemplates that the exhaust assembly 54 can be configured to actively or passively control the amount of gas exhausting to atmosphere. For example, if the pressure in the patient circuit falls, the exhaust assembly can open to provide a large, direct access for the patient to ambient atmosphere. The present invention also contemplates providing the exhaust assembly in seal member 36 alone or in combination an exhaust assembly in conduit coupling member 38. Finally, the exhaust assembly can also be omitted if exhausting gas from the system is not needed, which is typically the case in a dual-limb patient circuit configuration.

In addition to central portion 50, support member 34 includes a cheek mount support 70 disposed on opposite sides of and extending from the central portion. More specifically, a first cheek mount support 70a is provided on the right side of the central portion and a second cheek mount support 70b is provided on the left side of the central portion of support member 34. The central portion of the support member and the cheek mount supports are configured such that a pocket, cup, or receptacle 58 is defined at central portion 50. Receptacle 58 receives seal member 36 in a mated or matching relationship to assist in snugly holding the seal member to the support member.

Coupling and/or aligning seal member 36 to support member 34 is also assisted by providing openings 62 on each side of central portion 50. Openings 62 are sized and configured to mate with coupling members 44. The present invention contemplates that coupling members 44 and the associated openings 62 can have a variety of shapes, sizes, and configurations. Also, the relationship between coupling members 44 and the associated openings 62 can be reversed, for example with the coupling member or protrusion being provided on support member and an opening or a receptacle being provided on the seal member.

In addition, a protrusion 64 is provided that extends from opening 48 at the central portion of the support member. Protrusion 64 is sized and configured to insert into opening 46 of seal member 36 to provide an airtight coupling between the seal member and the support member. The present contemplates that protrusion 64 and the associated opening 46 can have a variety of shapes, sizes, and configurations. Also, the relationship between protrusion 64 and the associated opening 46 can be reversed, for example with the protrusion extending from seal member to insert into an opening 48 provided in the support member.

In the illustrated exemplary embodiment, each cheek mount support 70 has a first end 72 coupled to central portion 50 of support structure 34 and a second end 74. A headgear coupling element 75 is provided at second end 74 of each cheek mount structure. In the illustrated exemplary embodiment, headgear coupling element 75 is a slot 77 defined in the end portion of the cheek mount support. See FIG. 3. A headgear assembly 79 attaches to support structure 34 by inserting a portion of a headgear strap 81 through the slot and fasting the free end of the headgear strap to the rest of the strap, for example, using a hook and loop fastener. While a slot is shown, the present invention contemplates that any mechanism or structure for coupling a headgear assembly, and, in particular, a headgear strap to support member 34 can be used.

In the illustrated embodiment, first end 72 is coupled to central portion 50 as a unitary structure such that the cheek mount supports and the central portion are a single component. The present invention contemplates selectively coupling the cheek mount support to the central portion so that the each cheek mount support 70 and be removed and replaced. The present invention also contemplates rotatably coupling the cheek mount support to the central portion, for example, by providing a pivot connection at first end 72. In addition, one or both of the cheek mount supports 70 can be adjustably coupled to the central portion, that the effective length of the lateral portions of the support structure can be adjusted to suit the user's facial features.

Each cheek mount support includes an first member 76 and a second member 78, which, in the illustrated embodiment, are coupled at first end 72 and second end 74 of the cheek support member. In this manner, each cheek mount support 70 has a loop-shaped structure having an opening 80 defined between the first and second members. The present invention contemplates forming cheek support member from a flexible, semi-rigid, or rigid material serving as a frame. The present invention further contemplates that each cheek support member can include a pad provided between the frame and the surface of the user. This pad can be formed from any suitable material such as a silicone, foam, plastic, rubber, gel or a combination thereof.

Figure 4:
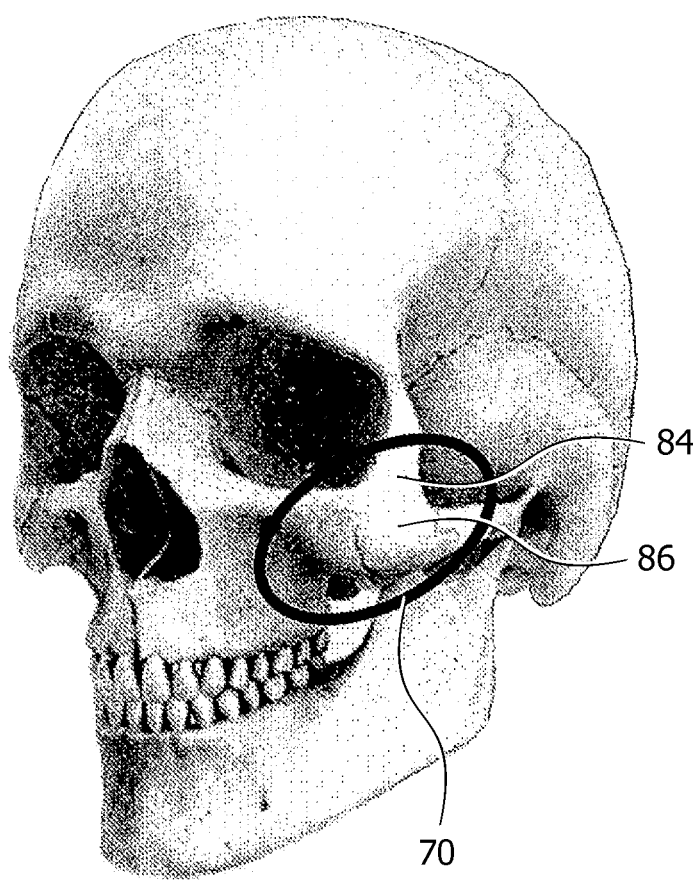
FIG. 4 is a perspective view of a human skull illustrating how the patient interface device of the present invention is positioned relative to the facial bones when worn by a user.

As best shown in FIGS. 3 and 4, each cheek support member 70, and, in particular, the first and second members and their interconnections that define the loop-shaped structure, are sized and configured such that when patient interface device 30 is worn by the user, the loop-shaped member is configured to be disposed over opposing sides a user's cheekbone while not being disposed over an apex of such a user's cheekbone. Stated another way, zygomatic bone (aka, cheekbone) 84 has a peak portion 86, i.e., a portion that protrude the furthest from the face. No part of cheek mount support 70 applies a force against peak portion 86 of the cheekbone. Instead, the peak portion of the cheek bond protrudes through opening 80 of cheek support mount 70 so that first member 76 and second member 78 rest on either side of the cheekbone. In the illustrated embodiment, cheek support member 70 fully encircles, but does not pass over the apex of, a user's cheek area 82. Each cheek mount support is configured to apply a force a side a user's cheekbone while applying substantially no force over an apex of such a user's cheekbone when the patient interface device being worn by a user.

The spacing between first member 76 and second member 78, i.e., the width of opening 80, as indicated by dimension D1 in FIG. 1 ranges from _____ to _____. The spacing between first end 72 and second end 74, i.e., the length of opening 80, as indicated by dimension D2 in FIG. 2 ranges from _____ to _____. This range of dimensions ensures that the components of cheek mount support 70 remain over the sides cheekbone but are not disposed over the apex of the cheekbone. As a result, the checkbone and overlying tissue becomes a support structure for holding the patient interface device in place on the face. Using opening 80 to "capture" or "anchor" to the cheekbone also provides for easy alignment of support member 34 on the user's face and enhances the stability of the support member of the face, and thereby decreasing leaks and patient discomfort.

It can thus be appreciated that the cheekbones act as both a locator and stabilizer of the patient interface device on the face. Providing a cheek support mount that substantially surrounds the apex of the patient's cheek bone, allows the patient interface device to anchor to the user utilize patient's prominent raised cheek bone structure to anchor the device to the face.

Figure 5:
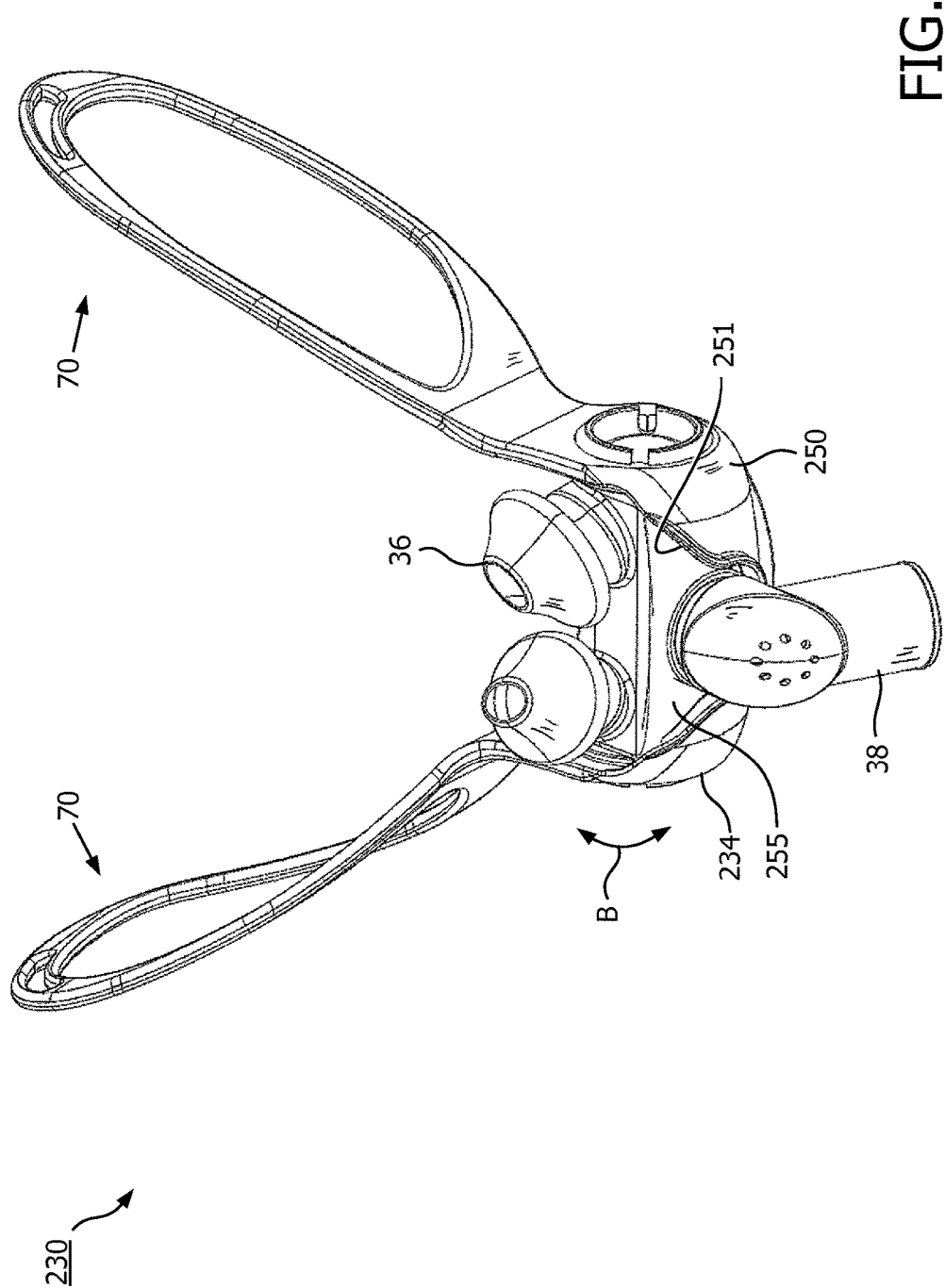
FIG. 5 is front perspective view of a patient interface device according to a second embodiment of the present invention.
Figure 6:
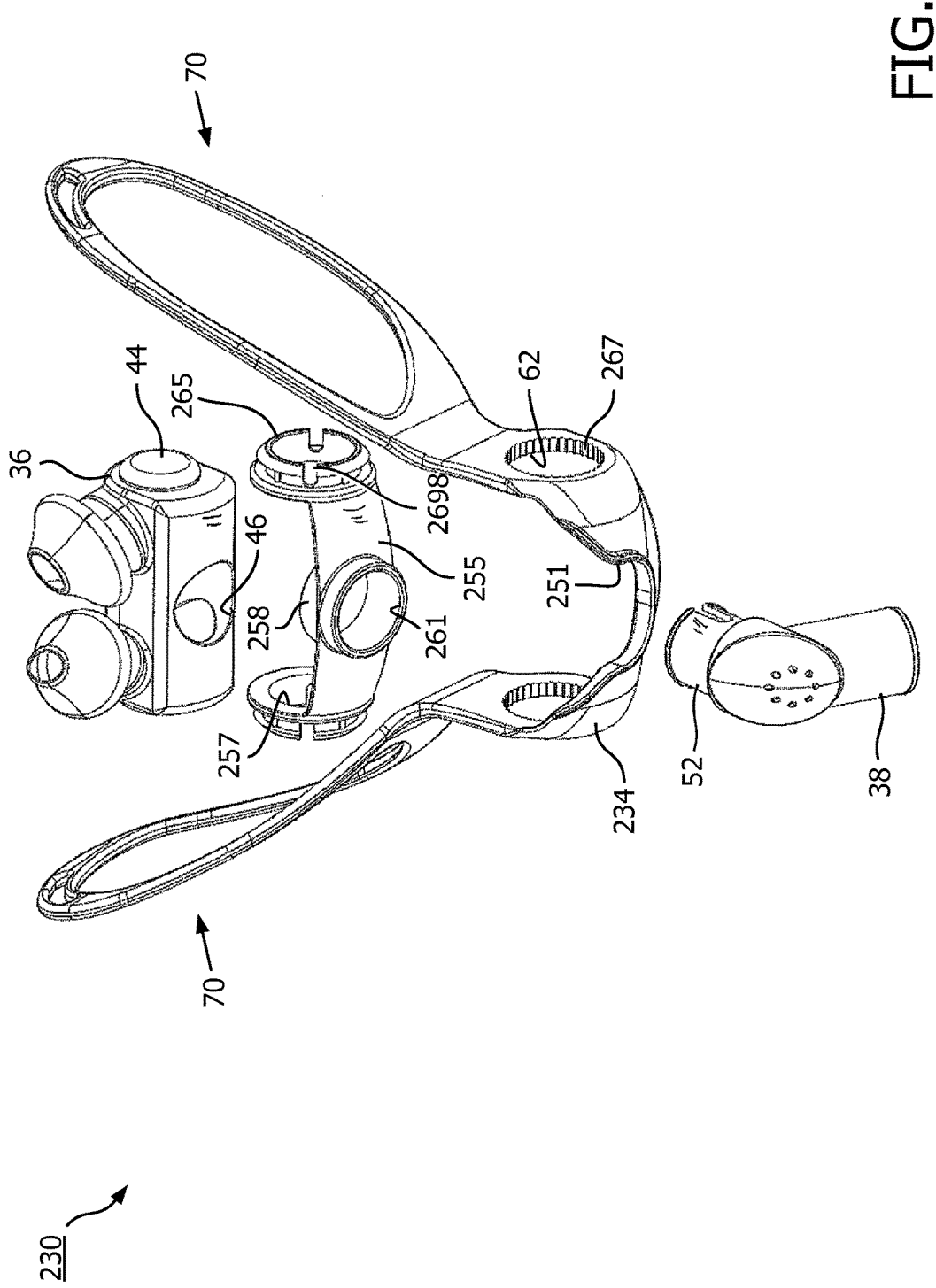
FIG. 6 is an exploded view of the patient interface device of FIG. 5.

FIGS. 5 and 6 illustrate a patient interface device 230 according to a second embodiment of the present invention. In this embodiment, patient interface device 230 is generally similar to that shown in FIGS. 1-2 except for the configuration of a central portion 250 of a support member 234. In this exemplary embodiment, a cutout 251 is provided in central portion 250 of a support member 234. In addition, an adjustment member 255 is provided between seal support member 234 and seal member 36.

Seal member 36 is coupled to adjustment member 255, for example, by locating coupling members 44 within openings 257 provided at each end of the adjustment member. In addition, a protrusion 259 that extends from an opening 261 in adjustment member 255 inserts into opening 46 of seal member 36 to provide a gas flow to the seal member. Connecting portion 52 of conduit coupling member 38 couples to opening 261.

Adjustment member 255 includes a ratchet member 265 at each end that inserts into opening 62 in support member 235. A number of teeth 267 are provided around the perimeter of opening 62 to engage protrusions 269 provided on a corresponding surface of ratchet member 265. This configuration for patient interface device 230 allows sealing member and adjustment member to rotate within the recess of the support member as indicated by arrow B. This pivoting movement allows the "angle of attack" of the nasal prongs to be adjusted to suit the facial features of the user. By providing cutout 251 both conduit coupling member 38 and seal member 36 can move together.

Figure 7:
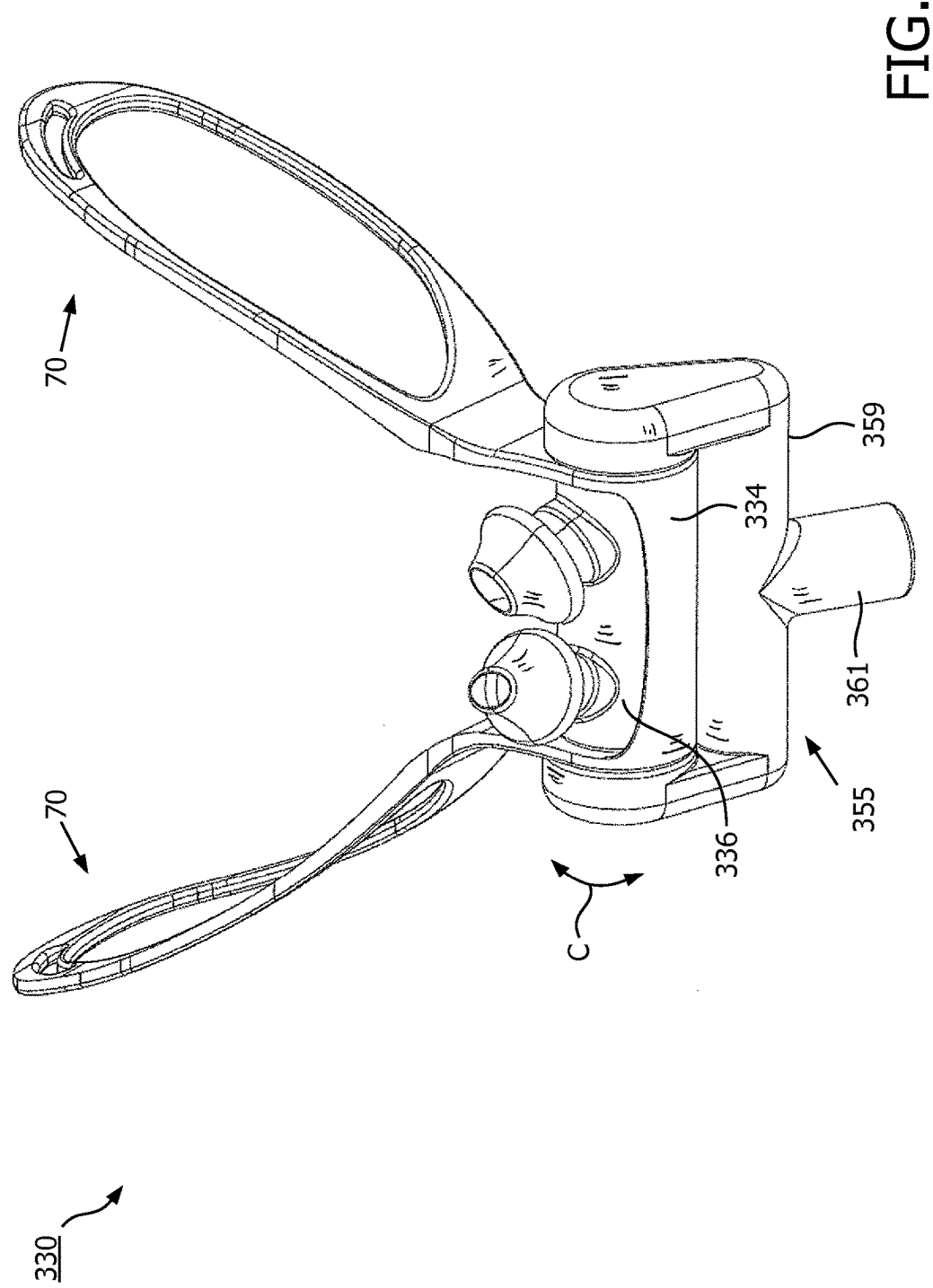
FIG. 7 is front perspective view of a patient interface device according to a third embodiment of the present invention.
Figure 8:
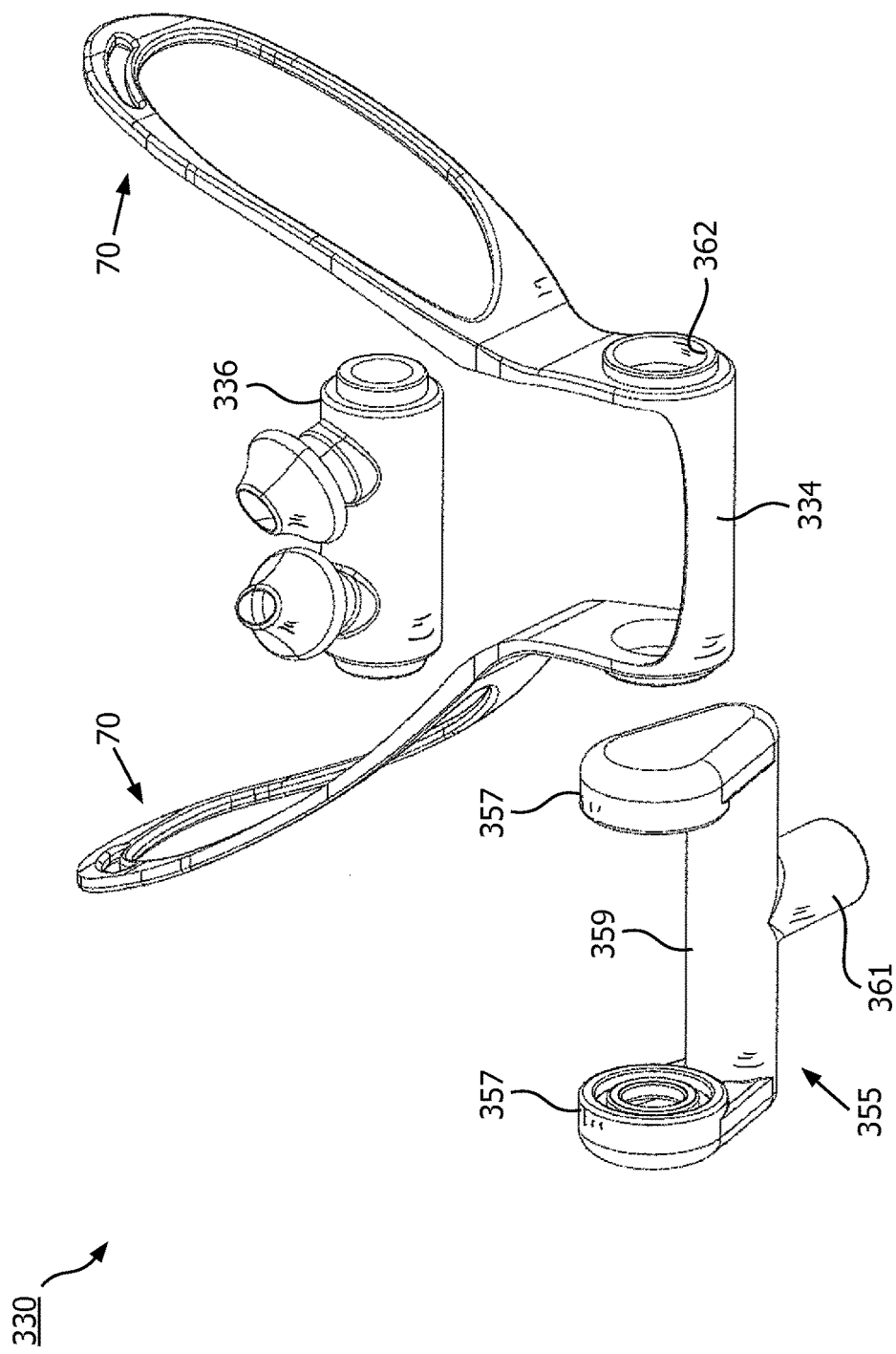
FIG. 8 is an exploded view of the patient interface device of FIG. 7.

FIGS. 7 and 8 illustrate a patient interface device 330 according to a third embodiment of the present invention. In this embodiment, patient interface device 330 is again generally similar to that shown in FIGS. 1-2. This embodiment, however, shows yet another technique for providing rotational adjustment of a seal member 336 relative to a support member 334, as indicated by arrow C, using another configuration for a conduit coupling member 355.

As in the previous embodiments, a central portion 350 of a support member 334 receives seal member 336. Instead of connecting to a central portion of the seal member, conduit coupling member 355 connects to each end of the seal member. More specifically, conduit coupling member 355 includes end connectors 357 coupled to a central housing 359. A conduit attaching portion 361 extends from the central housing for coupling to a patient circuit. Conduit coupling member 355 is configured such that gas provided to conduit attaching portion 361 is carried to the seal member 336 through central housing 359 and end connectors 357.

Each end connector 357 is connected to a respective end of seal member 336 via an opening 362 provided in support member 334. End connectors 357 and seal member 336 are configured to rotate relative to support member 334 while also providing a fluid connection therebetween. This configuration is advantageous over that shown in FIGS. 5 and 6, for example, in that it provides a wider degree of movement for the sealing member relative to the support member. The present invention contemplates configuring end connectors 357 and/or seal member 336 so that movement of these components is controlled, such as by providing a friction fit with the support member. Alternatively, end connectors 357 and/or seal member 336 can be configured to rotate freely relative to the support member.

Figure 9:
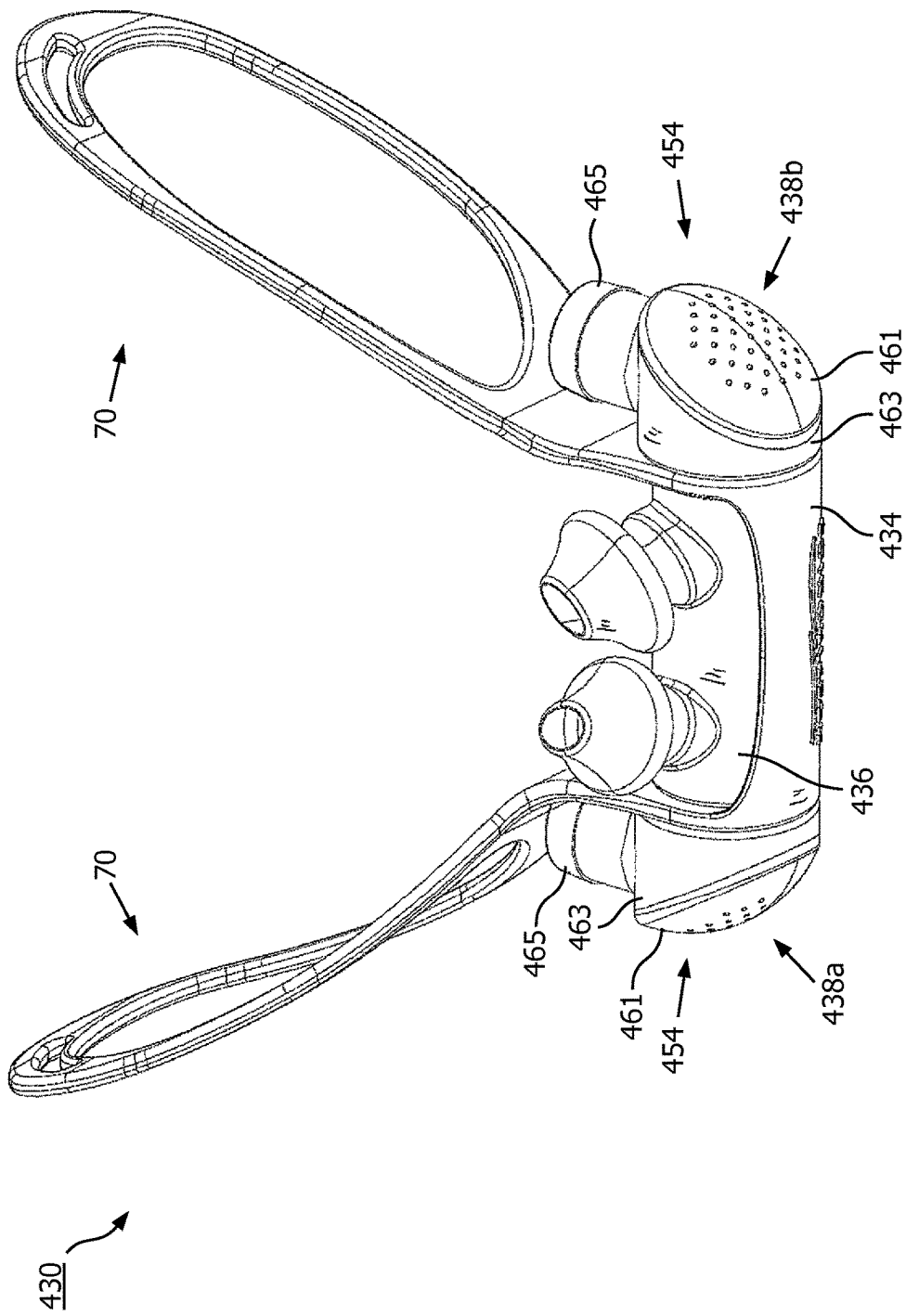
FIG. 9 is front perspective view of a patient interface device according to a fourth embodiment of the present invention.
Figure 10:
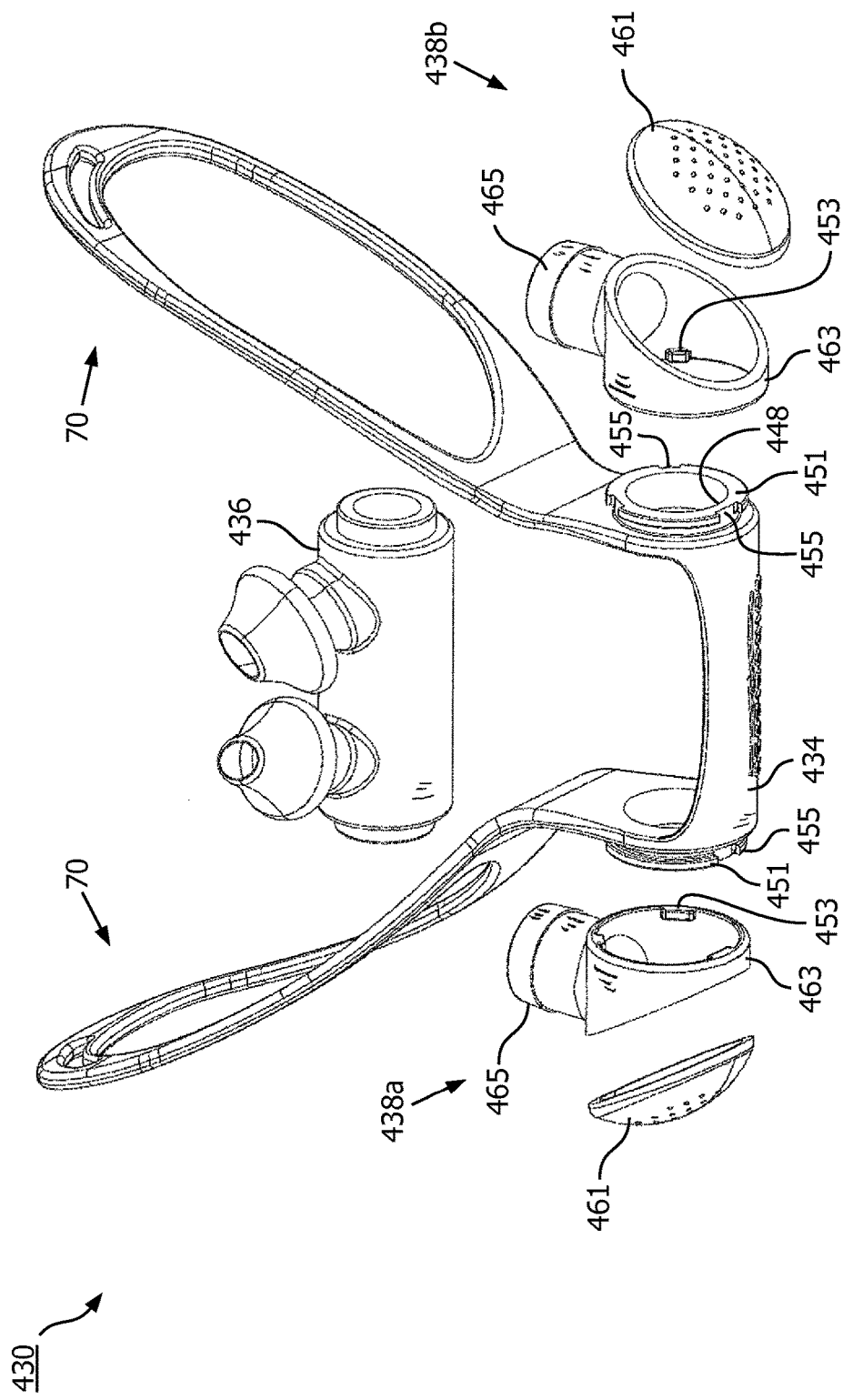
FIG. 10 is an exploded view of the patient interface device of FIG. 9.

FIGS. 9 and 10 illustrate a patient interface device 430 according to a fourth embodiment of the present invention. In this embodiment, patient interface device 430 is generally similar to that shown in FIGS. 7-8, except that in this embodiment, two gas flow paths are provided that couple to a patient circuit. More specifically, a first conduit coupling member 438*a* is provided on a first side of a seal member 436 and a support member 434 and a second conduit coupling member 438*b* is provided on a second side of seal member 436 and support member 434. First and second conduit coupling members 438*a* and 438*b* can be connected to a common patient circuit or they can be connected to a separate patient circuit.

Conduit coupling members 438*a* and 438*b* are elbow conduits having a first end that is adapted to be coupled to an openings 448 defined in support member 434 such that the patient circuit connector is rotatable relative to the support member. In an exemplary embodiment, the conduit coupling member is selectively attachable to support member 434, but it may also be permanently affixed thereto and need not be rotatably attached. Support member 434 includes a connection element 451 that engages a portion of an associated conduit coupling member. Tabs 453 and recesses 455 provided in each conduit coupling member and the associated connection element 451 serve to coupled the conduit coupling members 438*a* and 438*b* to support member 434.

In the illustrated exemplary embodiment, each conduit coupling member 438*a* and 438*b* includes an exhaust assembly, generally indicated at 454, to allow gas, such as the patient's exhaled carbon dioxide, to exhaust to the ambient atmosphere. Exhaust assemblies 454 can have any suitable configuration, such as one or more vent holes provided in the wall of conduit coupling member 438*a*, 438*b* and can be configured to actively or passively control the amount of gas exhausting to atmosphere.

In this embodiment, conduit coupling member 438*a*, 438*b* are formed from two components, such as an exhaust element 461 and an elbow element 463 being joined. The joining of exhaust element 461 and elbow element 463 can be permanent or these elements can be selectively attachable to one another. This latter configuration is advantageous in that it allows the exhaust assembly to be replaced. Finally, conduit coupling member 438*a*, 438*b* include a patient circuit connecting portion 465 to couple to the patient circuit.

Figure 11:
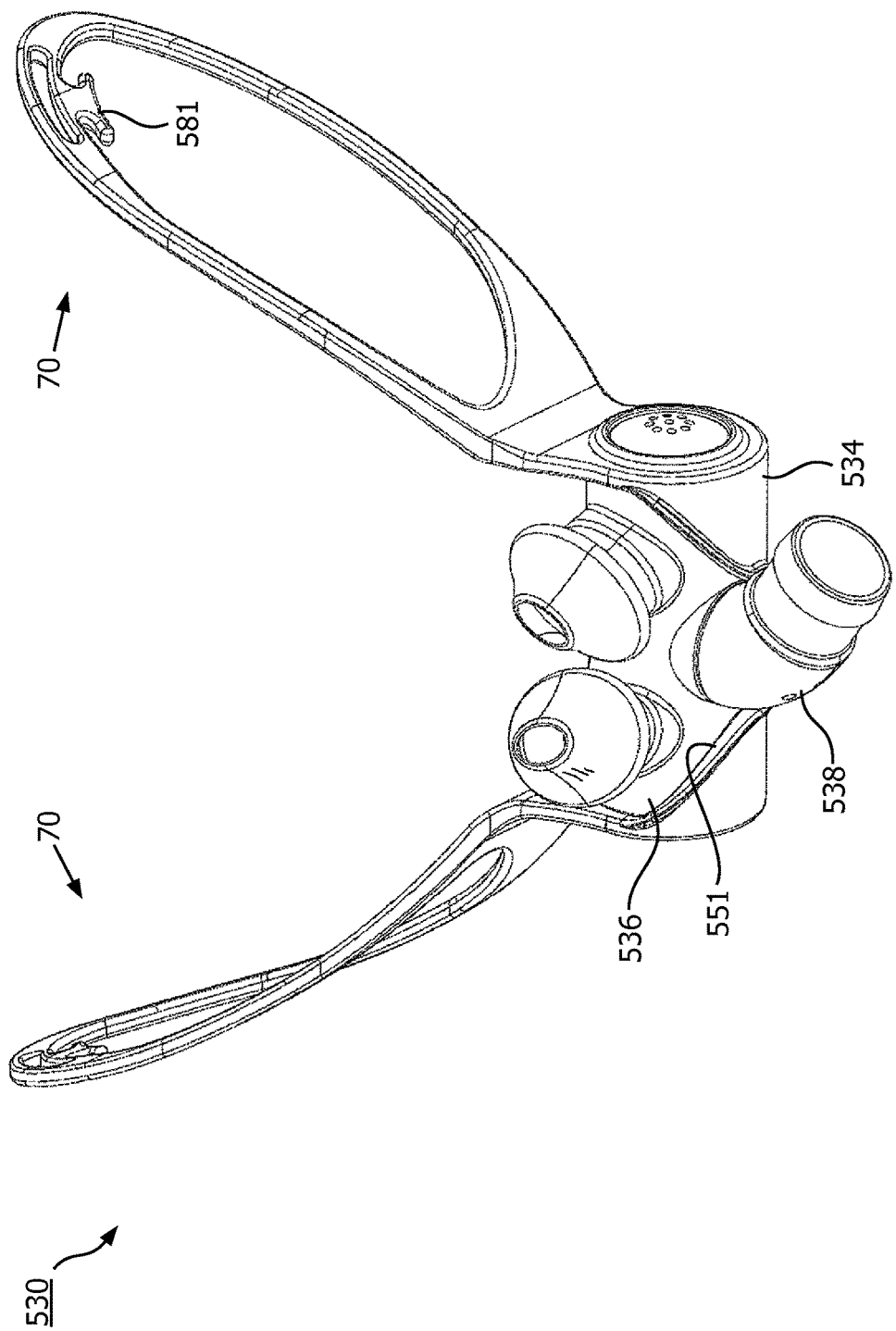
FIG. 11 is front perspective view of a patient interface device according to a fifth embodiment of the present invention.
Figure 12:
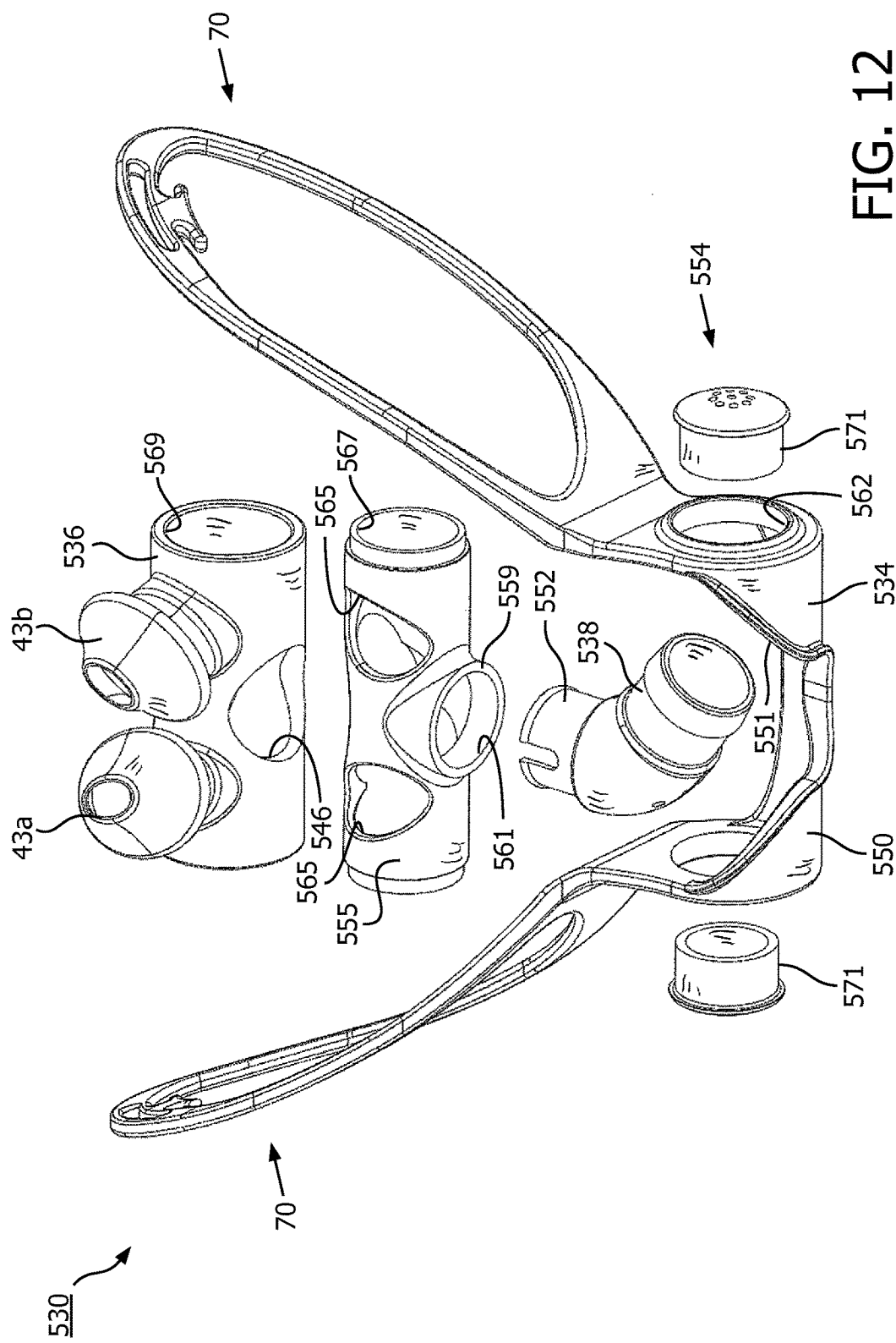
FIG. 12 is an exploded view of the patient interface device of FIG. 11.

FIGS. 11 and 12 illustrate a patient interface device 530 according to a fifth embodiment of the present invention. In this embodiment, patient interface device 530 is generally similar to that shown in FIGS. 5-6. As in the embodiment of FIGS. 5-6, patient interface device 530 includes a cutout 551 provided in central portion 550 of a support member 534. In addition, an adjustment member 555 is provided between a seal support member 534 and a seal member 536.

Seal member 536 is coupled to adjustment member 555, for example, by the seal member, which is formed from a generally flexible material, being disposed over the adjustment member, which is formed from a generally rigid or semi-rigid material. In addition, the present invention contemplates providing a protrusion 559 that extends from adjustment member 555 and inserts into an opening 546 of seal member 536 to provide a gas flow to the seal member. A connecting portion 552 of a conduit coupling member 538 couples to opening 561. Openings 565 are also provided in adjustment member 555 to provide a gas flow communication path between a hollow central portion of adjustment member 555 and nasal prongs 43*a* and 43*b*.

Openings 567 are provided in adjustment member 555 and 569 are also provided in seal member 536 that are coaxially aligned when the components of the patient interface device are assembled. These openings are also aligned with an opening 562 provided in support member 534. An exhaust assembly element 571 is provided in opening 562. An exhaust assembly, generally indicated at 554, is provided on one or both of exhaust assembly elements 571.

This embodiment also includes a protrusion 581 disposed at a second end 575 of cheek mount support 70. Protrusion 581 functions as a cleat to which a headgear straps attaches, thereby providing an alternative technique for attaching the headgear strap to the patient interface device.

Figure 13:
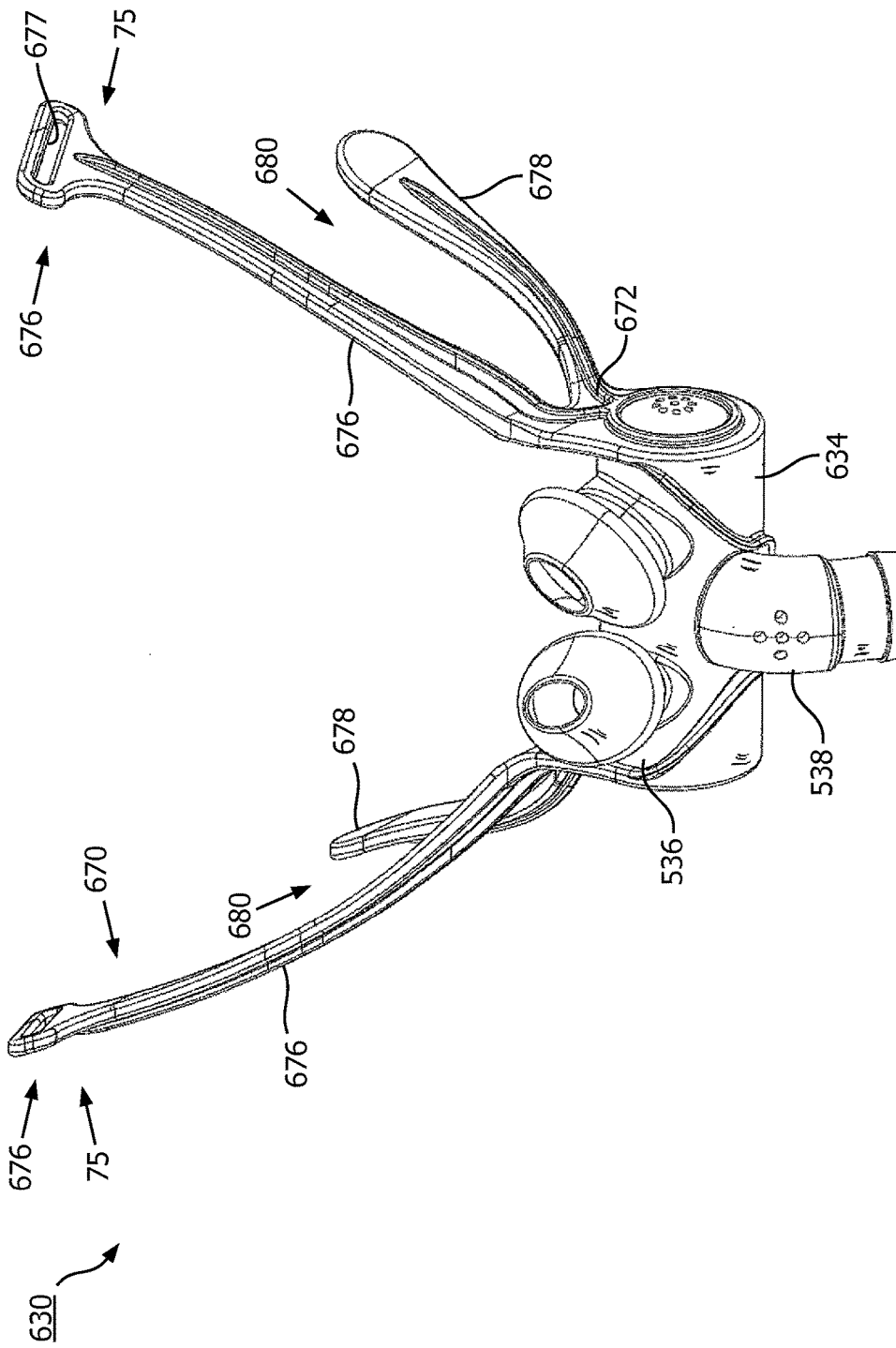
FIG. 13 is front perspective view of a patient interface device according to a sixth embodiment of the present invention.
Figure 14:
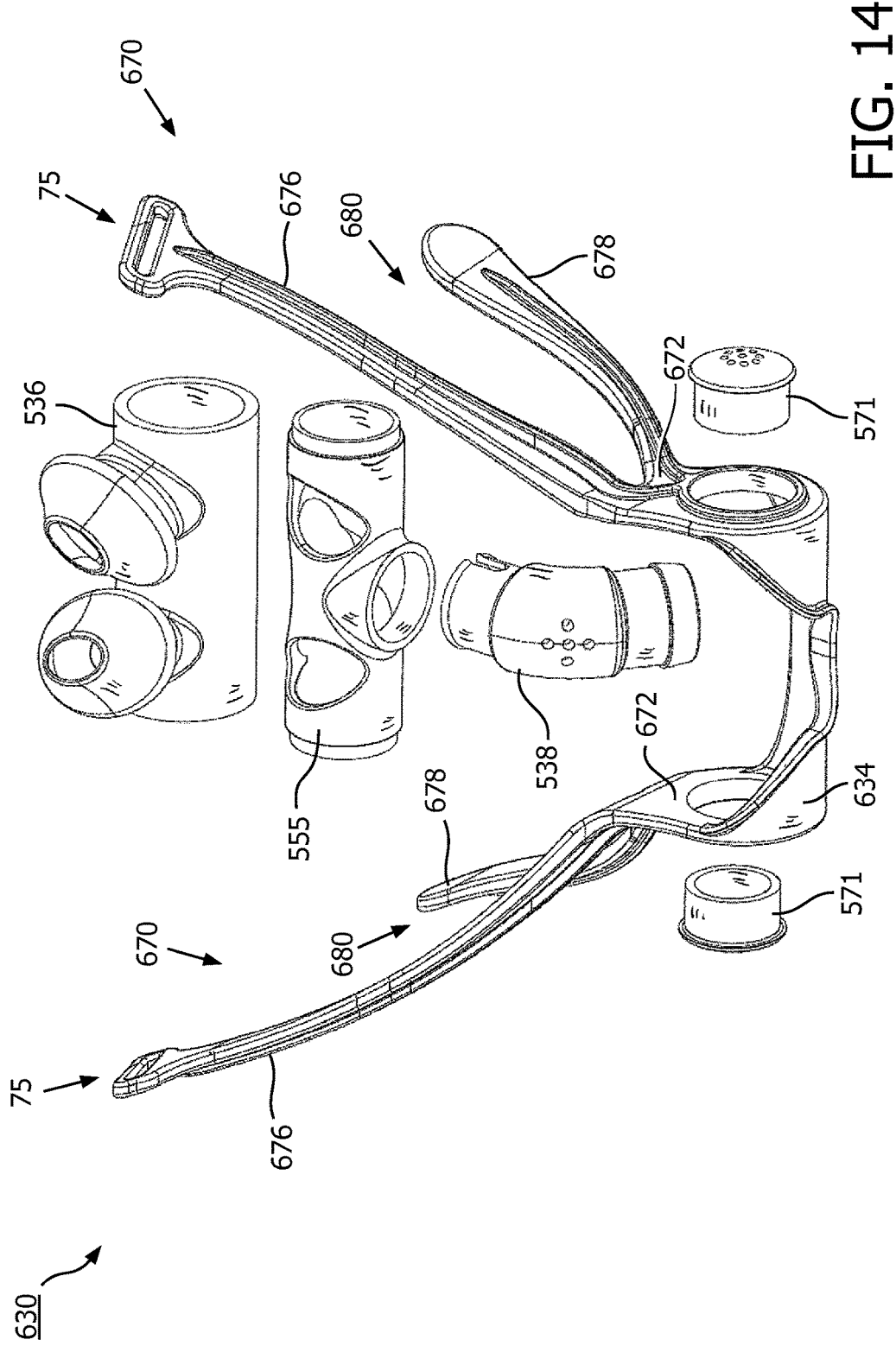
FIG. 14 is an exploded view of the patient interface device of FIG. 13.

FIGS. 13 and 14 illustrate a patient interface device 630 according to a sixth embodiment of the present invention. In this embodiment, patient interface device 630 is generally similar to that shown in FIGS. 11-12, except for a cheek mount support 670, which has a somewhat different configuration, yet provides the same function as the cheek mount support of the previous embodiment. This embodiment clarifies that the cheek mount support need not fully encircle the apex of the cheek bone.

In this exemplary embodiment, cheek mount supports 670 include a first end 672 coupled to a central portion 650 of support structure 634. Each cheek mount support 670 includes an first member 676 and a second member 678, which, in the illustrated embodiment, are coupled at first end 672 of the cheek support member. Unlike the other embodiments, a second of first member 676 and second member 678 are not coupled to one another. As a result, each cheek mount support 670 has a U-shaped configuration having an opening 680 defined between the first and second members. As in the previous embodiments, first and second members 676 and 678 distribute the strapping force onto the sides of the cheek area, but avoids providing the strapping force over the apex of the cheek bone. Also, this configuration for first member 676 and second member 678 serves to "clamp" or align the patient interface device to the face of the user using the cheekbone as a locating structure.

Figure 15:
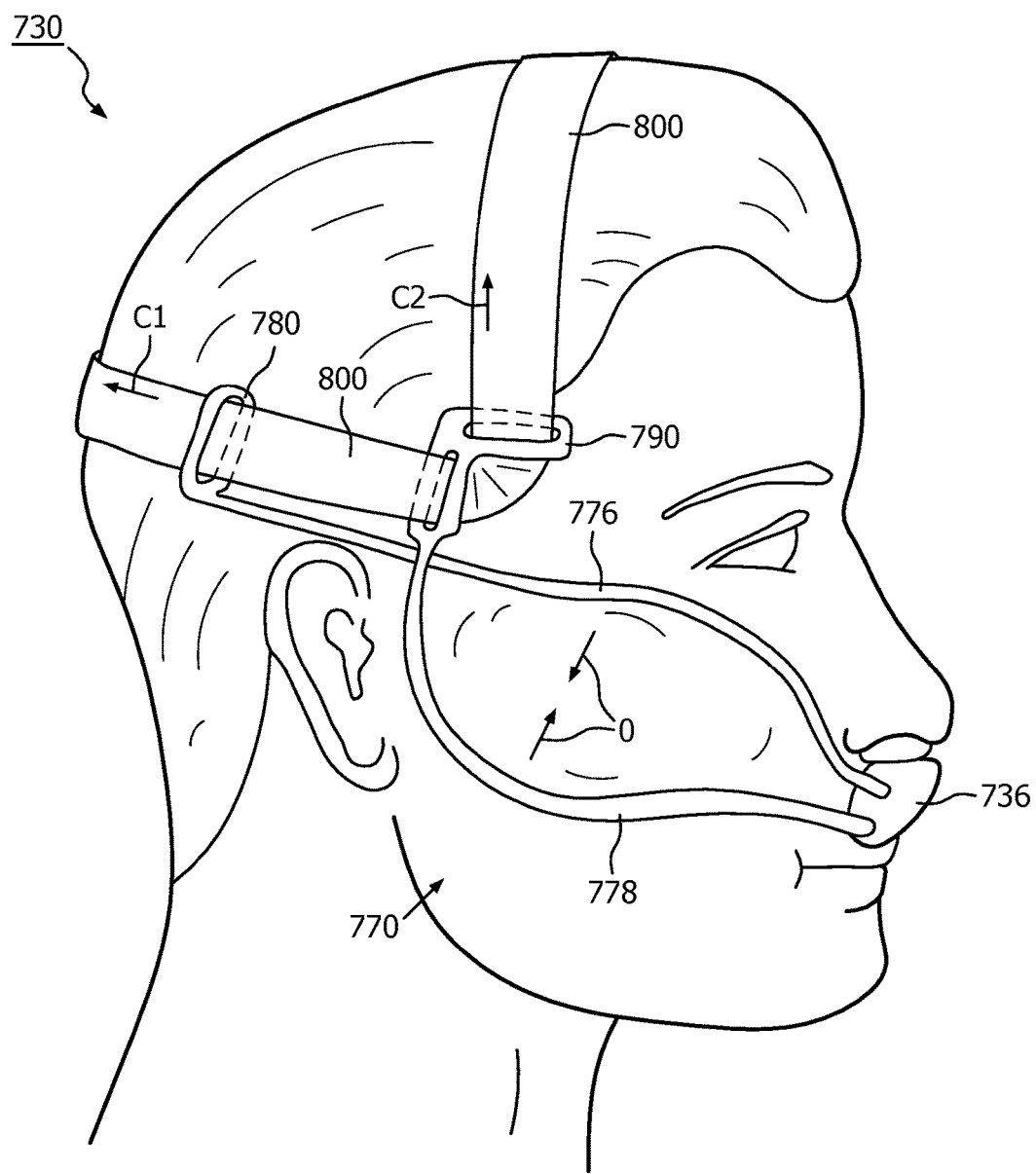
FIGS. 15 and 16 are side view of a patient interface device according to a seventh embodiment of the present invention shown worn by a user and showing alternative adjustments for the cheek mounting support.
Figure 16:
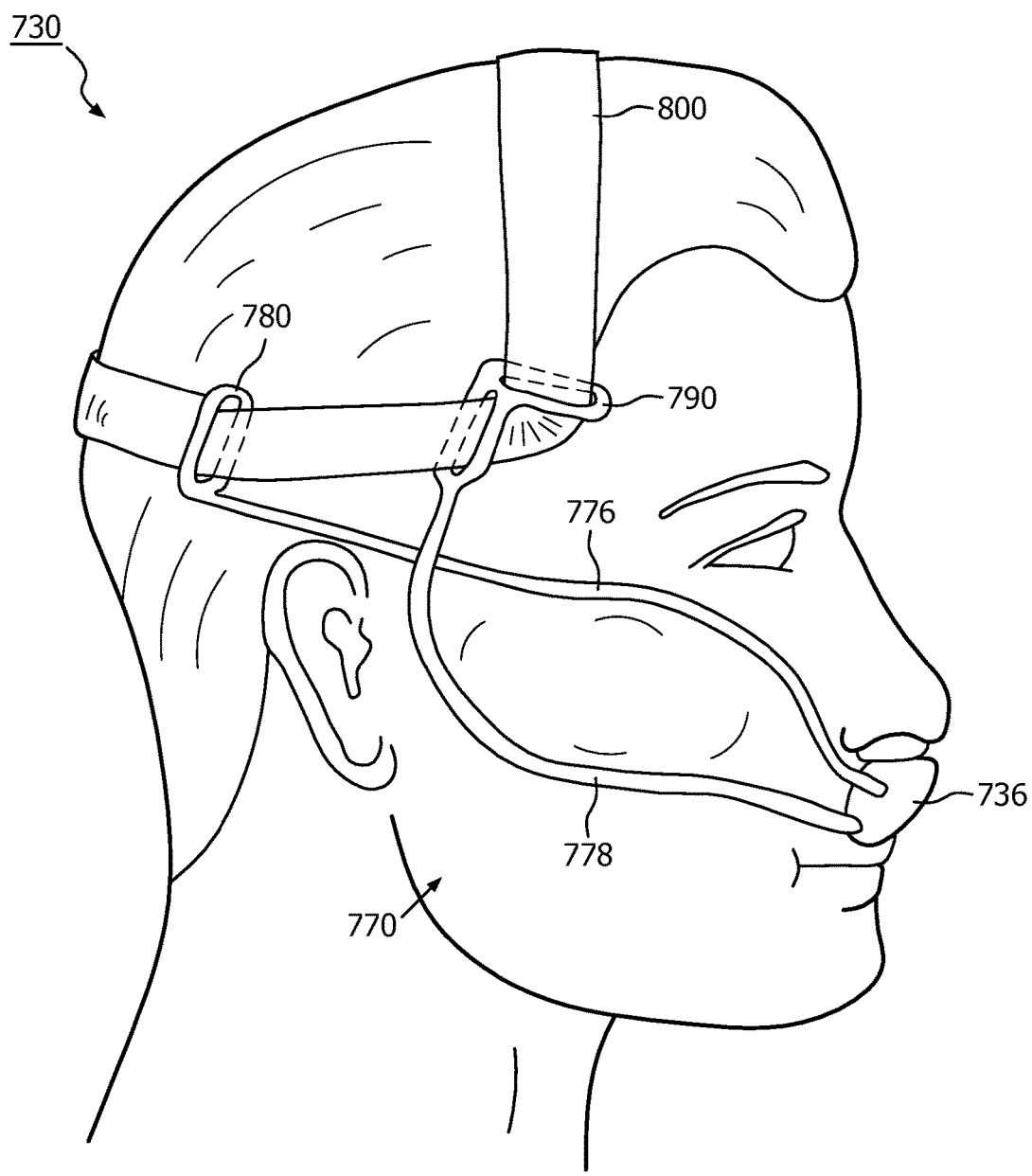

A headgear coupling element 75 is provided at second end 674 of first member 676. In the illustrated exemplary embodiment, headgear coupling element 75 is a slot 677 defined in the end portion of the cheek mount support FIGS. 15 and 16 illustrate a patient interface device 730 according to a seventh embodiment of the present invention. In this embodiment, patient interface device 730 includes a seal member 736 and a cheek mounted support 770 coupled to the seal member. Although not shown in this embodiment, a patient circuit provides a flow of gas to seal member 736, which includes a pair of nasal prongs that couples to an airway of the user.

Each cheek mounted support 770 includes a frame-like structure having a first member 776 and a second member 778 that cooperate to form a border partially or wholly surrounding the patient's cheek bone, and being supported thereby as described in connection with the cheek support member of the previous embodiments. First member 776 and second member 778 are configured to provide a "sissor" like configuration that can be actively or passively adjusted to accommodate a wide range of face and cheek structures. First member 776 and second member 778 are formed form a sufficiently rigid material, such as metal or plastic, so that they retain their shape when the sissor-like adjustment is made.

More specifically, an end portion 780 of first member 776 is coupled to a headgear strap 800 so that it is slideably adjustable along a length of the headgear strap. Similarly, an end portion 790 of first member 778 is coupled to headgear strap 800 so that it is slideably adjustable along a length of the headgear strap. In the illustrated embodiment, end portion 790 includes a pair of loops disposed at an angle with respect to one another. As end portions 780 and 790 are moved apart, as indicated by arrows C1 and C2, first member 776 and a second member 778 in a cheek area move toward one another, as indicated by arrows D. This embodiment represents one of variety of techniques for adjusting the cheek mount support to suit the facial features of the user and/or allow the user to adjust the fit to suit his or her whim.

The patient interface device of the present invention can support any style of nasal or nasal/oral cushion, i.e., seal member coupled with a rigid, semi-rigid, or flexible mask frame, i.e., support member, that includes a cheek mount support that engages the side or lateral portions cheekbone. The cheekbones act as both a locator and stabilizer of the mask on the face. A patient interface device utilizing the cheekbone supported platform provides greater stability and comfort than alternative masks and improves all aspects of alternative mask features, including ease of initial fitting, ease of adjustment, ease of removal/installation of the mask, stability, comfort, and aesthetics, thereby increasing customer compliance.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device comprising:
    a headgear assembly;
    a support member comprising a central support portion and a pair of cheek mount supports extending from respective opposite sides of the central support portion, wherein the central support portion and the cheek mount supports are a unitary structure made of a generally rigid material consisting of metal, plastic, or a combination thereof, wherein the central support portion defines a seal member receptacle, wherein each cheek mount support comprises a first member and a second member spaced from the first member, wherein the first member and the second member in each cheek mount support are joined at both a first end and a second end to define a loop-shaped structure that is sized and configured to be disposed about a cheekbone of a user entirely forward of an ear of the user, wherein a spacing between the first member and the second member in each cheek mount support in a direction that is orthogonal to a longitudinal axis of the cheek mount support ranges from 1 cm to 8 cm, wherein a spacing between the first end and the second end ranges from 1 cm to 12 cm, wherein in each cheek mount support at least a portion of the first member and at least a portion of the second member do not extend toward one another and instead extend in first and second parallel planes, respectively, that are parallel to the longitudinal axis such that the spacing between the at least a portion of the first member and the at least a portion of the second member is constant, and wherein the second end of each cheek mount support includes a headgear coupling element structured to receive a strap of the headgear assembly;

a seal member received in a mated or matching relationship in the seal member receptacle to hold the seal member to the support member, wherein the seal member is adapted to seal against a surface of the user to communicate a flow of gas with an airway of the user; and a conduit coupling member operatively coupled to the seal member.

2. The device of claim 1, wherein the seal member includes a pair of nasal prongs.

3. The device of claim 1, further comprising a pad disposed on a surface of the cheek mount support for contacting a user responsive to the device being worn by the user.

4. The device of claim 1, wherein the central support portion includes first and second openings provided on opposite sides of receptacle, wherein the first opening is mated with a first coupling member of the seal member and second opening is mated with a second coupling member of the seal member.

5. The device of claim 1, wherein the seal member is rotatably coupled to the receptacle of the support member.

6. The device of claim 1, wherein the conduit coupling member is operatively coupled to a central portion or a side portion of the seal member.

7. The device of claim 1, further comprising an exhaust assembly associated with the seal member, the conduit coupling member, or both.

8. The device of claim 1, wherein the spacing between the first member and the second member in each cheek mount support in the direction that is orthogonal to the longitudinal axis of the cheek mount support ranges from 2 cm to 6 cm.

9. The device of claim 1, wherein the spacing between the first end and the second end ranges from 2 cm to 10 cm.

10. The device of claim 1, wherein each headgear coupling element comprises a slot provided in the cheek mount support.

11. A method of donning a patient interface device, wherein the patient interface device includes a seal member and a support member that includes a central support portion and a pair of cheek mount supports extending from respective opposite sides of the central support portion, wherein the central support portion and the cheek mount supports are a unitary structure made of a generally rigid material consisting of metal, plastic, or a combination thereof, wherein the central support portion defines a seal member receptacle holding the seal member, wherein each cheek mount support comprises a first member and a second member spaced from the first member, and wherein the first member and the second member in each cheek mount support are joined at both a first end and a second end to define a loop-shaped structure defining an opening, the method comprising:

positioning the seal member against a nose of a patient to enable communication of a flow of gas to an airway of the patient through the seal member; and positioning one of the cheek mount supports in a manner wherein the opening defined by the loop-shaped structure is disposed completely forward of an ear of the patient and an apex portion of a zygomatic bone of the patient protrudes through the opening such that the first member and the second member rest on opposite sides of the zygomatic bone and such that the one of the cheek mount supports fully in circles but does not pass over the apex portion and no part of the one of the cheek mount supports applies a force directly against the apex portion.

* * * * *